United States Patent
Smith et al.

(10) Patent No.: US 6,728,561 B2
(45) Date of Patent: Apr. 27, 2004

(54) MULTISPECTRAL IMAGE PROCESSING METHOD, APPARATUS AND COMPUTER PROGRAM PRODUCT FOR DETERMINING THE BLOOD OXYGEN SATURATION IN A VESSEL

(75) Inventors: Matthew H. Smith, Madison, AL (US); Kurt R. Denninghoff, Birmingham, AL (US); Lloyd W. Hillman, Huntsville, AL (US); Raghunandan Manchenahalli, Santa Clara, CA (US)

(73) Assignee: University of Alabama in Huntsville, Huntsville, AL (US)

(*) Notice: Subject to any disclaimer, the term of this patent is extended or adjusted under 35 U.S.C. 154(b) by 0 days.

(21) Appl. No.: 10/217,797

(22) Filed: Aug. 13, 2002

(65) Prior Publication Data

US 2003/0088165 A1 May 8, 2003

Related U.S. Application Data

(60) Provisional application No. 60/312,187, filed on Aug. 14, 2001.

(51) Int. Cl.[7] ............................ A61B 5/00; G06K 9/00
(52) U.S. Cl. ...................... 600/323; 600/473; 600/476; 382/128
(58) Field of Search .................. 600/310, 322, 600/323, 336, 340, 473, 476; 382/128

(56) References Cited

U.S. PATENT DOCUMENTS

| | | | |
|---|---|---|---|
| 5,119,814 A | | 6/1992 | Minnich |
| 5,308,919 A | | 5/1994 | Minnich |
| 5,776,060 A | | 7/1998 | Smith et al. |
| 5,935,076 A | | 8/1999 | Smith et al. |
| 5,974,338 A | * | 10/1999 | Asano et al. ............ 600/323 |
| 6,244,712 B1 | | 6/2001 | Smith et al. |
| 6,276,798 B1 | * | 8/2001 | Gil et al. ............ 351/206 |

2002/0188203 A1  12/2002  Smith et al.

OTHER PUBLICATIONS

Kuntimad, G. et al., *Perfect Image Segmentation Using Pulse Coupled Neural Networks,* IEEE Transactions on Neural Networks, vol. 10, No. 3, May 1999, pp. 591–598.

Chaudhuri, S. et al., *Detection of Blood Vessels in Retinal Images Using Two–Dimensional Matched Filters,* IEEE Transactions on Medical Imaging, vol. 8, No. 3, Sep. 1989, pp. 263–269.

Tolias, Y. A. et al., *A Fuzzy Vessel Tracking Algorithm for Retinal Images Based on Fuzzy Clustering,* IEEE Transactions on Medical Imaging, vol. 17, No. 2, Apr. 1998, pp. 263–273.

Zana, F. et al., *A Multimodal Registration Algorithm of Eye Fundus Images Using Vessels Detection and Hough Transform,* IEEE Transactions on Medical Imaging, vol. 18, No. 5, May 1999, pp. 419–428.

(List continued on next page.)

*Primary Examiner*—Eric F. Winakur
(74) *Attorney, Agent, or Firm*—Alston & Bird LLP

(57) ABSTRACT

Methods, apparatus and computer program products are provided for more accurately determining the percent transmittance of a vessel, such as a retinal vessel, at each of a number of different wavelengths and, in turn, for more accurately determining the blood oxygen saturation within the vessel. The blood oxygen saturation is determined based upon a plurality of images of the vessel obtained with illumination of different wavelengths. Background images are generated based upon respective images of the vessel in order to approximate the tissue bed underlying the vessel, such as the background fundus underlying the retinal vessel. Thereafter, a plurality of transmittance images are determined based upon respective pairs of the background images and the images of the vessel, such as by dividing the image of the vessel by the respective background image. Based upon a plurality of transmittance images, the blood oxygen saturation in the vessel may be determined.

49 Claims, 10 Drawing Sheets

OTHER PUBLICATIONS

Hoover, A. et al., *Locating Blood Vessels in Retinal Images by Piecewise Threshold Probing of a Matched Filter Response,* IEEE Transactions on Medical Imaging, vol. 19, No. 3, Mar. 2000, pp. 203–210.

Beach, J. M. et al., *Oximetry of Retinal Vessels by Dual-Wavelength Imaging: Calibration and Influence of Pigmentation,* American Physiological Society, 1999, pp. 748–758.

* cited by examiner

MULTISPECTRAL IMAGE PROCESSING METHOD, APPARATUS AND COMPUTER PROGRAM PRODUCT FOR DETERMINING THE BLOOD OXYGEN SATURATION IN A VESSEL

CROSS-REFERENCE TO RELATED APPLICATIONS

The present application claims priority from U.S. Provisional Application No. 60/312,187 filed Aug. 14, 2001 by Matthew H. Smith, et al., the contents of which are incorporated herein in their entirety.

FEDERALLY SPONSORED RESEARCH OR DEVELOPMENT

The United States Government may have rights in the inventions set forth herein as provided by the terms of Contract No. DAMD17-98-1-8007 awarded by the U.S. Medical Army Research and Materials Command and Contract No. NOOO14-99-1-0226 awarded by the Office of Naval Research.

FIELD OF THE INVENTION

The present invention relates generally to methods, apparatus and computer program products for measuring blood oxygen saturation in a vessel, such as a retinal vessel and, more particularly, to methods, apparatus and computer program products for processing images of a vessel, such as a retinal vessel, obtained with light of different wavelengths to obtain a more accurate measurement of the percent transmittance of the vessel at each wavelength and, in turn, a more accurate measurement of the blood oxygen saturation of the vessel.

BACKGROUND OF THE INVENTION

A variety of spectroscopic oximetry techniques have been developed to monitor the blood oxygen saturation and blood oxygen content in vessels, such as retinal vessels. By monitoring the blood oxygen saturation, the arteriovenous oxygen difference can be determined as described by U.S. Pat. No. 5,308,919 to Thomas E. Minnich, U.S. Pat. No. 5,776,060 to Matthew H. Smith, et al., and U.S. Pat. No. 5,935,076 to Matthew H. Smith, et al. Based upon the arteriovenous oxygen difference, the cardiac output of a subject can be determined in order to assist in post-operative monitoring and the management of critically ill patients. By monitoring the blood oxygen saturation, the loss of blood can be detected, and the rate and quantity of blood loss over time can be estimated as described by U.S. Pat. No. 5,119,814 to Thomas E. Minnich.

In addition to the variety of invasive techniques that require blood to be drawn, oftentimes repeatedly, from a patient, a number of non-invasive spectroscopic oximetry techniques have been developed to measure the blood oxygen saturation of a patient without requiring blood to be drawn from the patient. For example, a number of non-invasive spectroscopic oximetry techniques have been developed which measure the blood oxygen saturation of a patient based upon the transmittance of the blood within a retinal vessel, such as a retinal vein or a retinal artery. For example, U.S. Pat. Nos. 5,776,060 and 5,935,076 describe techniques for measuring the oxygen saturation of blood within a retinal vessel by illuminating the retinal vessel with light having a combination of wavelengths and then measuring the transmittance of the blood within the retinal vessel in response to the illumination at each of the selected wavelengths. Based upon the respective transmittances of the blood within the retinal vessel that are measured at each of the selected wavelengths, the oxygen saturation of the blood within the retinal vessel can be determined. The contents of U.S. Pat. Nos. 5,776,060 and 5,935,076 are hereby incorporated by reference in their entirety.

While a retinal vessel can be illuminated with light of different wavelengths in a variety of manners, U.S. Pat. No. 6,244,712 which issued Jun. 12, 2001 to Matthew H. Smith, et al. describes an advantageous technique for alternately illuminating the posterior portion of an eye with the signals emitted by different lasers such that the resulting image has interlaced portions formed by signals returning from the posterior portion of the eye in response to illumination by different lasers. Since each laser is designed to emit signals having a different wavelength, the resulting image can therefore include data collected at each of a number of different wavelengths. The contents of U.S. Pat. No. 6,244,712 are also hereby incorporated by reference in their entirety.

While a retinal vessel can be illuminated by light having a variety of different wavelengths, at least one wavelength is generally in the red part of the spectrum. In this regard, the proper combination of wavelengths must be utilized in order to obtain data from which the transmittance of the blood and, in turn, the oxygen saturation of the blood within the retinal vessel can be determined. At least one of most any proper combination of wavelengths is typically in the red spectrum. Additionally, diode lasers are typically utilized as laser sources for illuminating a retinal vessel and a common wavelength of light emitted by a diode laser is in the red spectrum. Unfortunately, a retinal blood vessel absorbs light in the red spectrum relatively weakly compared to light having other wavelengths. As such, the signals in the red spectrum that are returning from the posterior portion of the eye will not exhibit as great a contrast between the retinal vessel and the underlying tissue bed, i.e., the background fundus, as signals having other wavelengths.

As described in U.S. patent application Ser. No. 10/134,360, the light with which a retinal vessel is illuminated may be reflected and transmitted in a variety of different manners. Of these different manners, single pass light that passes through the retinal vessel, diffuses laterally through the retinal and/or choroidal layers and then exits through the pupil without again traversing the retinal vessel contains the information relevant to determining the oxygen saturation of the blood in the retinal vessel. However, the other signals that have been reflected and transmitted in different manners contain information that is less useful and render the determination of the blood oxygen saturation more difficult. As such, an aperture may be disposed within the path of the optical signals returning from the eye in order to preferentially pass single pass optical signals while blocking optical signals that have been reflected and transmitted in other manners. While effective for preferentially passing single pass optical signals, the optical signals that pass through the aperture and are detected have a substantially lower intensity and contrast than the unfiltered optical signals returning from the posterior portion of the eye. U.S. patent application Ser. No. 10/134,360 was filed Apr. 29, 2002 by Matthew H. Smith, et al. and is incorporated herein in its entirety.

As a result of the reduced contrast exhibited by the optical signals having a wavelength in the red spectrum and the lower intensity and contrast of the single pass optical signals that are preferentially passed through the aperture, the resulting image may have a relatively low contrast and intensity, thereby rendering it difficult to distinguish the retinal vessel from the background fundus. This difficulty in distinguishing the retinal vessel from the background fundus is exacerbated since the coloration of the background fundus can vary significantly. As a result of the relatively low contrast between the retinal vessels and the background fundus, it is sometimes difficult to determine the percent transmittance of the retinal vessel and, in turn, the oxygen saturation of the blood within the retinal vessel with sufficient certainty.

Accordingly, it would be advantageous to develop improved methods and apparatus for determining the blood oxygen saturation within a vessel, such as a retinal vessel. In particular, it would be advantageous to develop improved methods and apparatus for evaluating the optical signals returning from the posterior portion of the eye in order to more reliably determine the percent transmittance of the retinal vessel in response to illumination by light of each of a number of different wavelengths and, in turn, to more precisely determine the blood oxygen saturation within the retinal vessel, especially in instances in which the resulting images have a relatively low contrast between the retinal vessel and the background fundus.

SUMMARY OF THE INVENTION

An improved method, apparatus and computer program product are therefore provided according to one aspect of the present invention for more accurately determining the percent transmittance of a vessel, such as a retinal vessel, at each of a number of different wavelengths and, in turn, for more accurately determining the blood oxygen saturation within the vessel. The method, apparatus and computer program product are particularly advantageous for determining the blood oxygen saturation within a retinal vessel from images having a relatively low contrast between the retinal vessel and a tissue bed, such as the background fundus, such as images resulting from the illumination of the retinal vessel with optical signals in the red spectrum and images that have been constructed from optical signals that have been filtered to preferentially pass single pass light. Methods are also provided according to other advantageous aspects of the present invention for generating background images of the tissue bed that underlies a vessel and for separating pixels representative of the tissue bed from pixels representative of a vessel.

According to one aspect, the method, apparatus and computer program product determine the blood oxygen saturation in a vessel based upon a plurality of images of the vessel that were obtained in response to illumination of the vessel with light of different wavelengths. In this regard, a plurality of background images are generated based upon respective images of the vessel. In order to generate the background images, an image of the tissue bed underlying the vessel is approximated from a respective image of the vessel. To generate the image of the tissue bed, the image of the vessel is processed to separate pixels representative of the vessel from pixels representative of the tissue bed. According to one aspect of the present invention, the pixels that formerly represented the vessel are then redefined based upon values of at least some of the pixels representative of the tissue bed, thereby creating the background image. In this regard, the pixels formerly representative of the vessel may be redefined by being scaled to have the same mean and standard deviation as the pixels representative of the tissue bed. Alternatively, the pixels formerly representative of the vessel may be redefined in accordance with curves that are fit based upon values of the pixels representative of the tissue bed that are on opposite sides of the vessel.

Thereafter, a plurality of transmittance images are determined based upon respective pairs of the background images and the images of the vessel. For example, each transmittance image can be determined by dividing the image of the vessel by the respective background image. Based upon the plurality of transmittance images, the blood oxygen saturation in the vessel may be determined. Additionally, an image of the blood oxygen saturation in the vessel may be generated.

A number of preliminary steps may be executed prior to generating the plurality of background images. In this regard, at least one vessel may be initially identified in each of the images of the vessel. The images of the vessel may then be registered or aligned with one another. As mentioned above, the plurality of images of the vessel may then be processed to separate pixels representative of the vessel from pixels representative of the tissue bed. While the images may be processed in various manners to separate pixels representative of the vessel from pixels representative of the tissue bed, the method of one advantageous aspect of the present invention examines the pixels of each image along lines extending across the vessel, such as in a direction perpendicular to the vessel. For each line of pixels, a threshold is determined based upon the values of the pixels along the line. For example, the threshold may be determined based upon at least one of a mean and a standard deviation of the values of the pixels along the respective line. In one embodiment, for example, the threshold x is determined as follows:

$$x = \bar{x} - \alpha \sigma_x$$

wherein $\bar{x}$ is the mean and $\sigma_x$ is the standard deviation of the pixels along the respective line, and wherein $\alpha$ is a predefined constant. Once the threshold is determined, the pixels are separated along each line into pixels representative of the vessel and pixels representative of the tissue bed depending upon the relationship of the threshold for the respective line to values of the pixels along the line.

Even once the pixels representative of the vessel have been separated from the pixels representative of the tissue bed, the method, apparatus and computer program product may further process and clean up each image. Within each image, for example, pixels determined to be part of the vessel but that are at least partially surrounded by pixels representative of the tissue bed may be redefined to now also be representative of the tissue bed. The plurality of images may also be processed to identify a pixel in one image that differs from a corresponding pixel in another image in its representation of that portion of the image as either the vessel or the tissue bed. If any such pixels are identified, one of the pixels may be redefined to be consistent with the other pixel. Still further, the plurality of images may also be processed to identify a group of adjacent pixels that each represent the vessel and to redefine any pixels that are also initially representative of the vessel but are remote from the group of adjacent pixels to be representative of tissue bed.

Based upon these processing techniques, relatively clean images of the vessel can be generated which, in turn, can be utilized to generate background images and transmittance images and, in turn, to determine the blood oxygen saturation in the vessel in an accurate fashion. Moreover, as described above, the method, apparatus and computer program product are particularly advantageous for determining the blood oxygen saturation within a retinal vessel from images having a relatively low contrast between the retinal vessel and the background fundus, such as images resulting from the illumination of the retinal vessel with optical signals in the red spectrum and images that have been constructed from optical signals that have been filtered to preferentially pass single pass light.

BRIEF DESCRIPTION OF THE DRAWINGS

Figure 1:
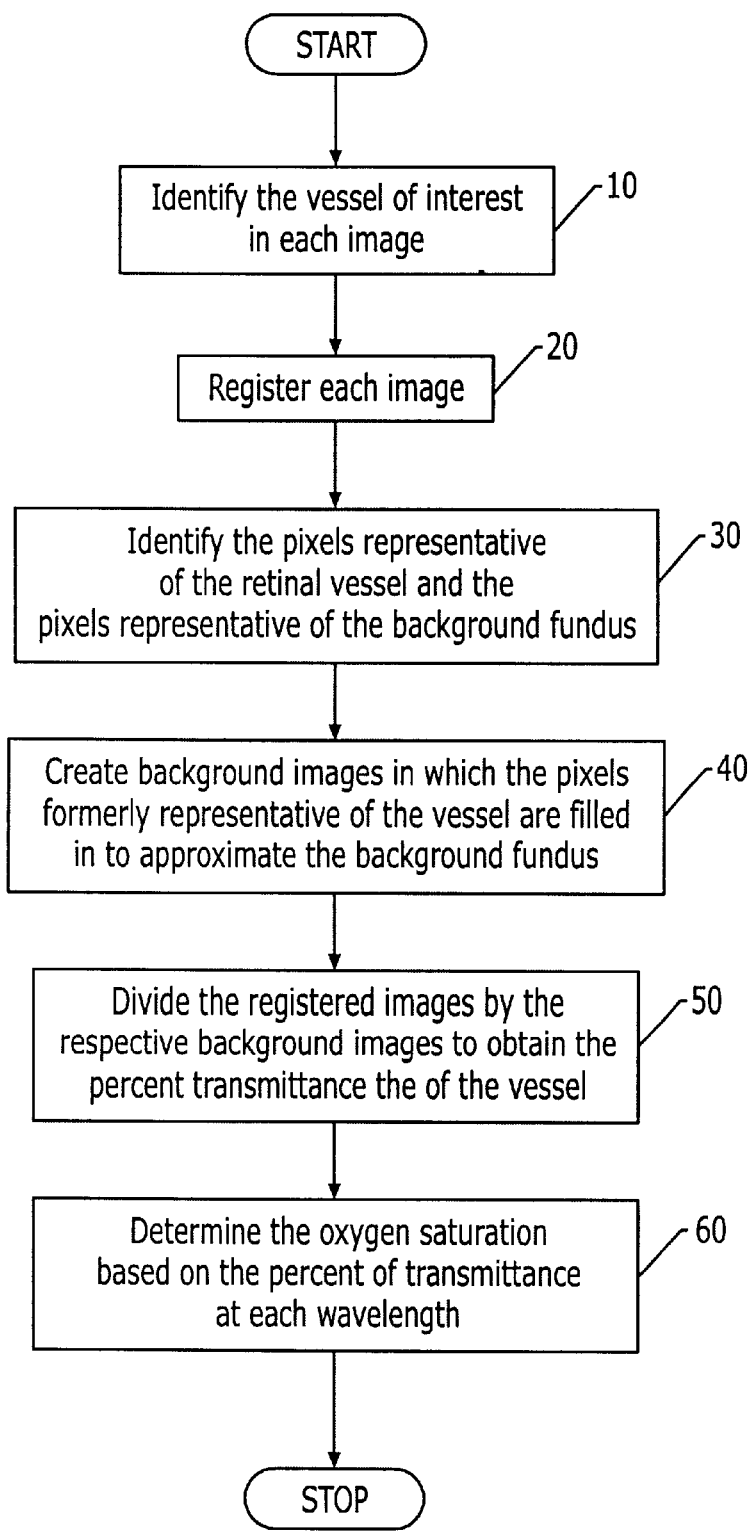
Figure 2:
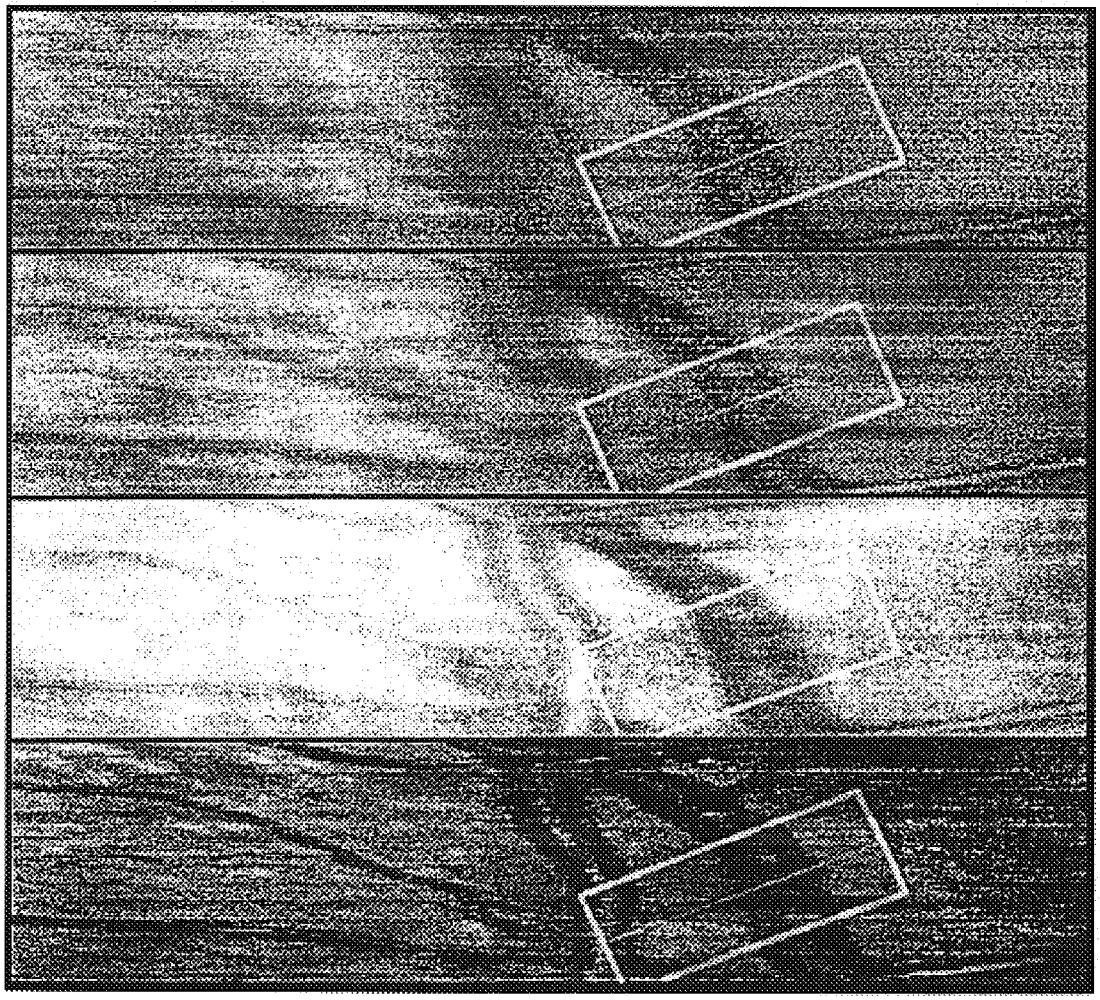
Figure 3:
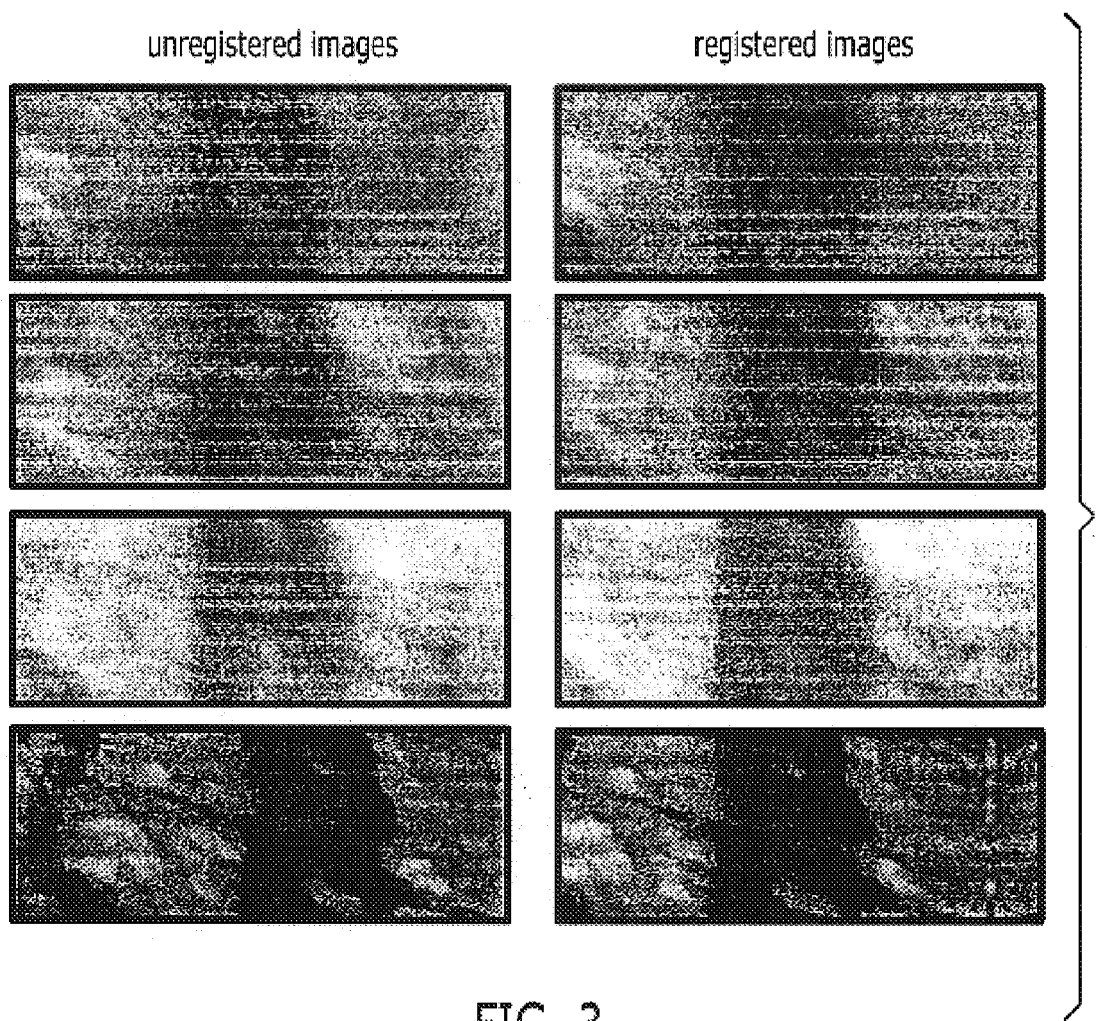
Figure 4:
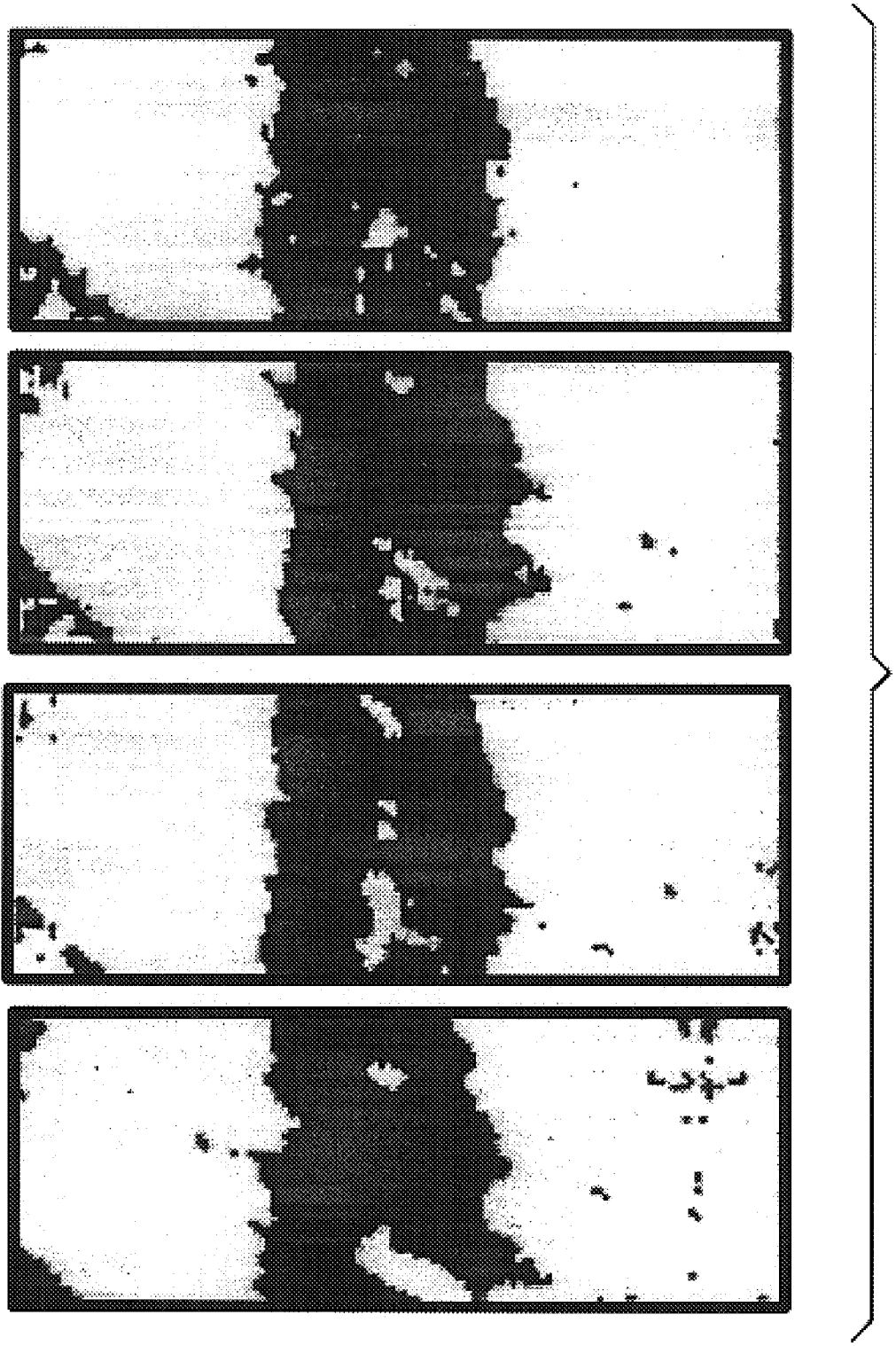
Figure 5:
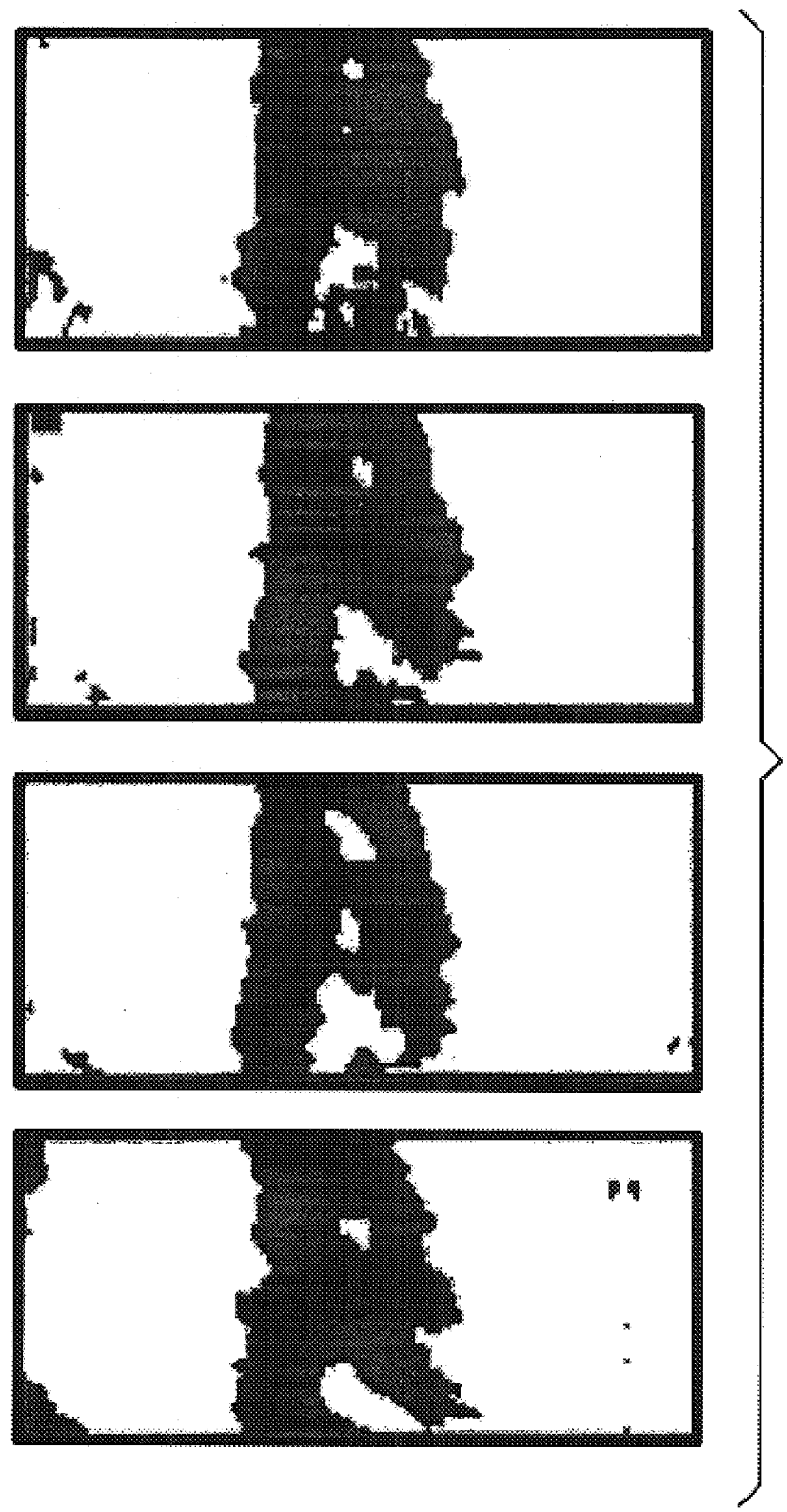
Figure 6:
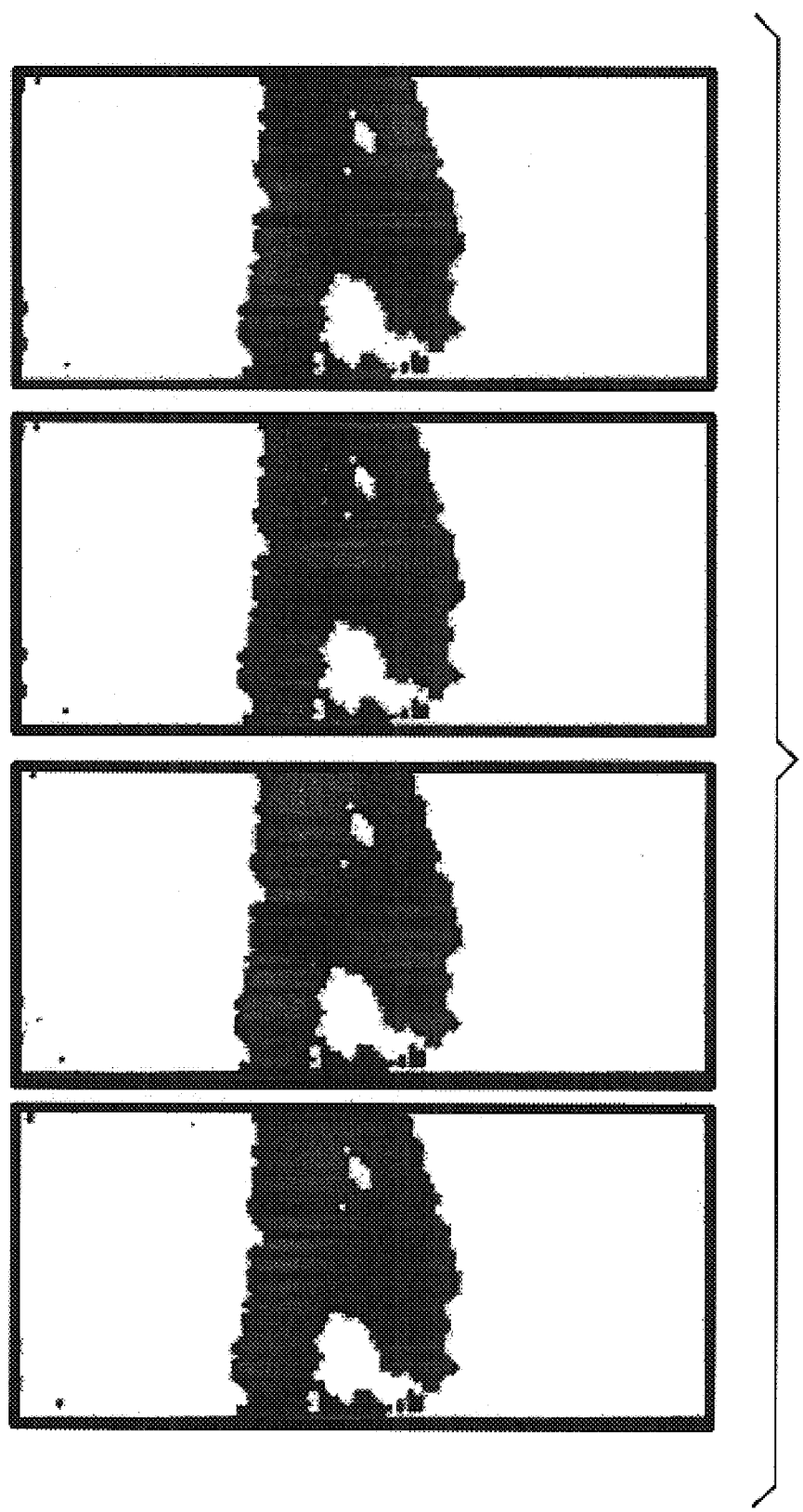
Figure 7:
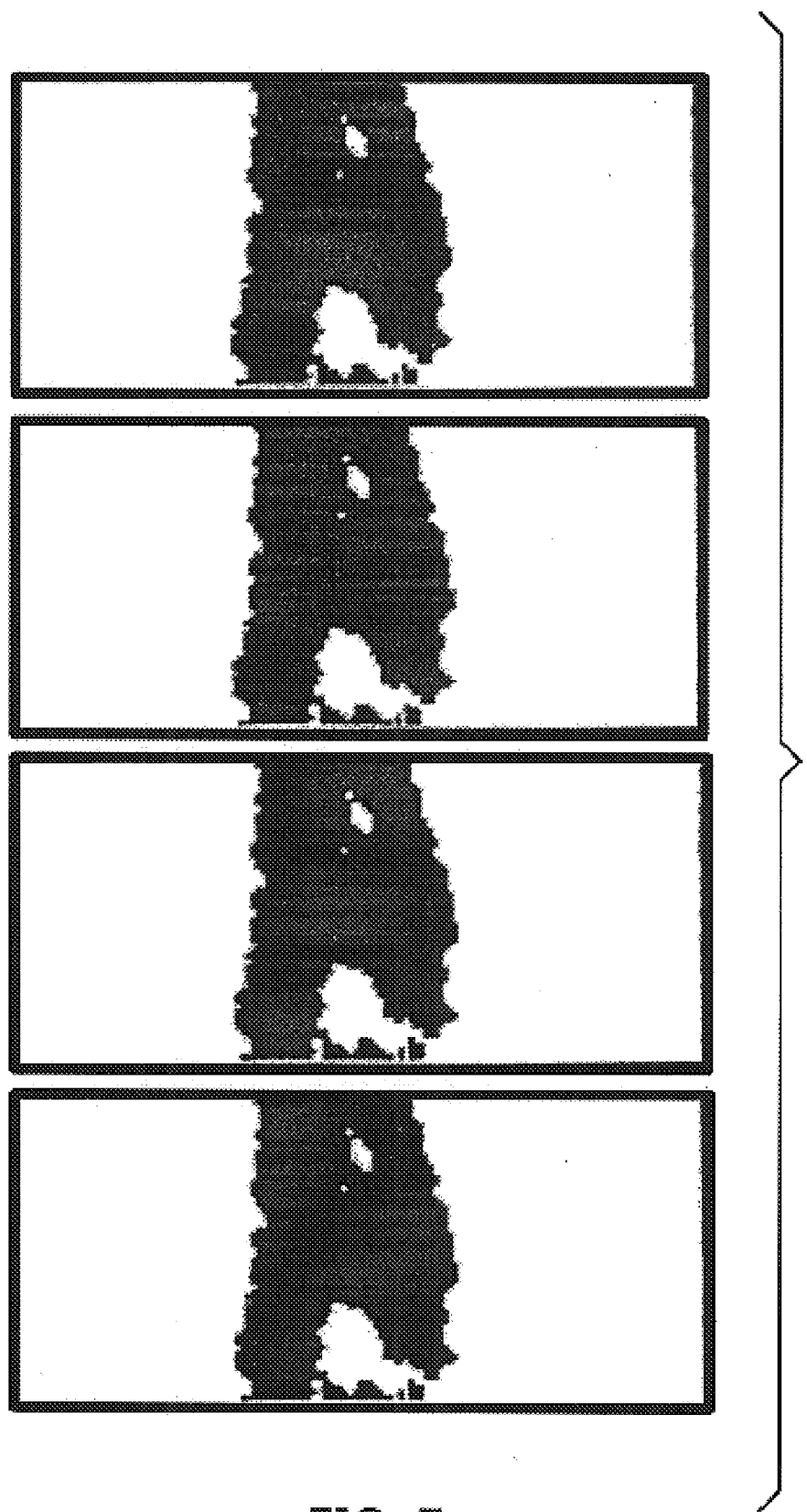
Figure 8:
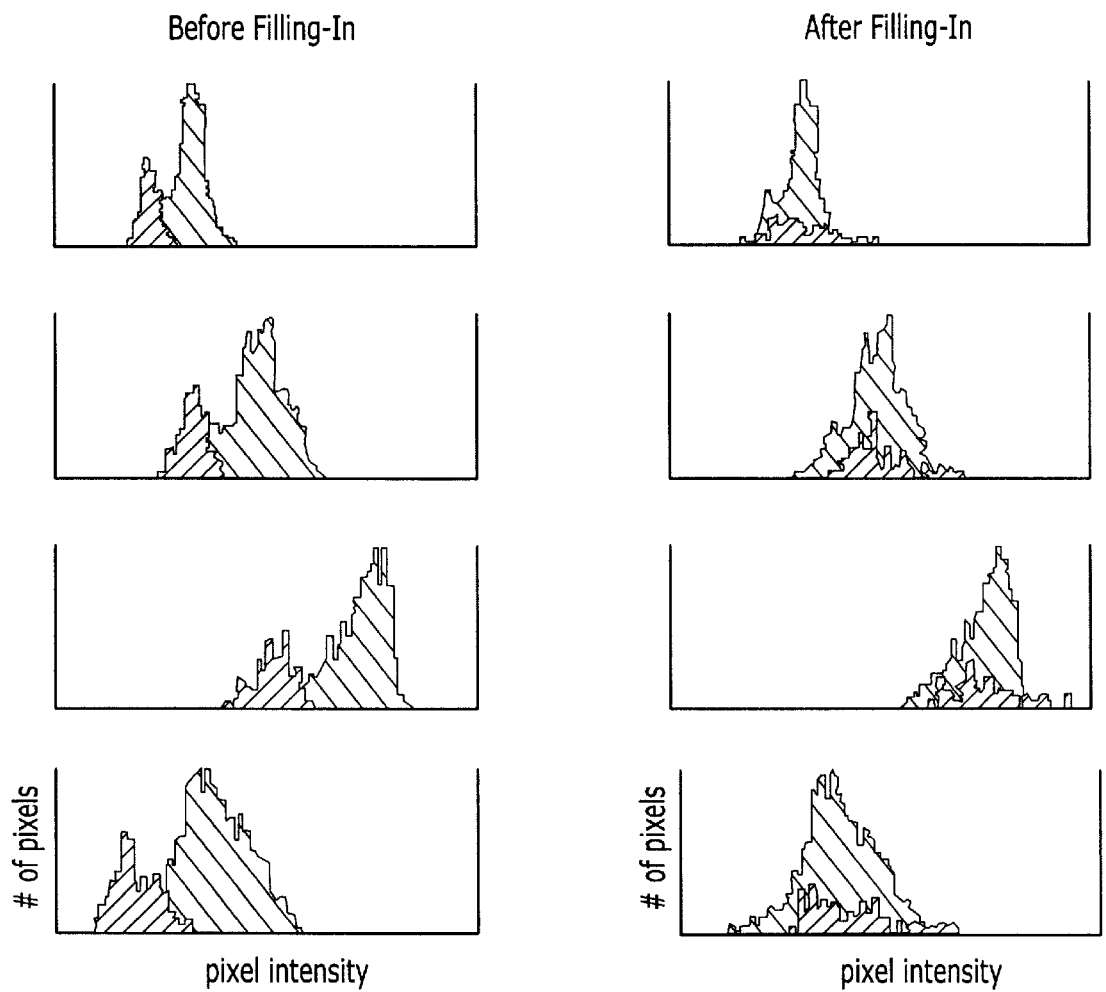
Figure 9:
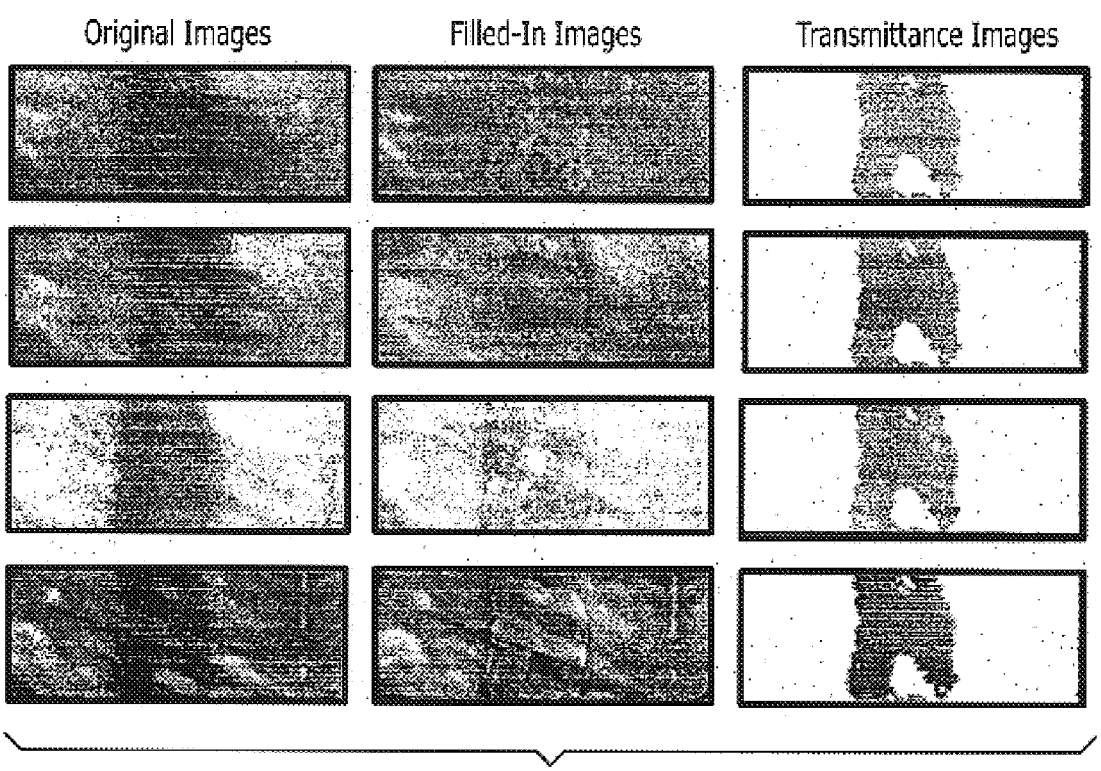
Figure 10:
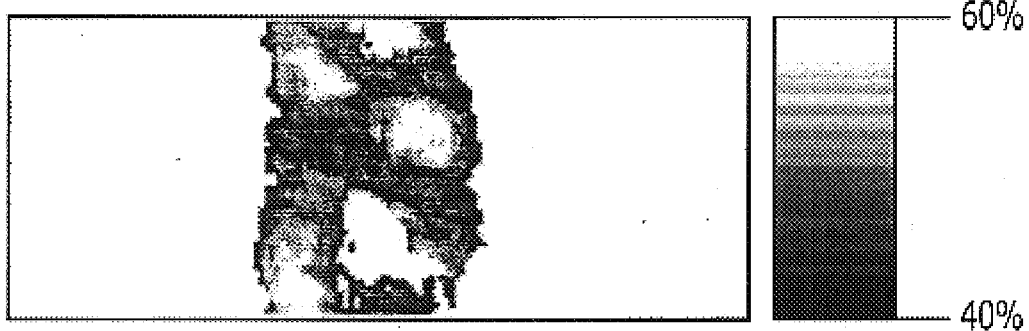

Having thus described the invention in general terms, reference will now be made to the accompanying drawings, which are not necessarily drawn to scale, and wherein:

FIG. 1 is a flow chart depicting the operations performed by the method, apparatus and computer program product according to one embodiment to the present invention;

FIG. 2 are four images acquired with light having four different wavelengths and optionally filtered to reduce the noise in which the white rectangles indicate regions identified for analysis;

FIG. 3 depicts the regions selected for analysis by the operator and bounded by the white rectangles in FIG. 2 in the left-hand column with corresponding images in the right-hand column following registration of the retinal vessels;

FIG. 4 depicts four images of the retinal vessel following the application of a line-by-line threshold to the registered images of FIG. 3;

FIG. 5 depicts four images of the retinal vessel following the application of further filtering to the thresholded images of FIG. 4;

FIG. 6 depicts four images of the retinal vessel following the application of a voting algorithm to the respective images of FIG. 5;

FIG. 7 depicts four images of the retinal vessel once the edges of the respective images of FIG. 6 have been cleaned;

FIG. 8 are intensity histograms of the pixels of each of the four images of a retinal vessel in which the black histograms are based upon pixels representative of the retinal vessel and the gray histograms are based upon pixels representative of the background fundus in which the distinction between the pixels representative of the retinal vessel and the background fundus is derived from FIG. 7 and in which the intensity histograms in the left-hand column are based upon pixel values from the registered images of FIG. 3 and the intensity histograms in the right-hand column are subsequent to filling in the retinal vessel such that the pixel values that were representative of the retinal vessel are scaled to have a mean and a standard deviation that are identical to the pixels representative of the background fundus;

FIG. 9 depicts four images of the retinal vessel in each of three states, namely, as a registered image as also shown in FIG. 3, as a filled-in image based upon the intensity histograms of the right-hand column in FIG. 8 and as transmittance images once the registered images have been divided by the filled-in images; and FIG. 10 is a depiction of the blood oxygen saturation of the retinal vessel on a pixel-by-pixel basis based upon the four transmittance images of FIG. 9.

DETAILED DESCRIPTION OF THE PRESENT INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

An improved method, apparatus and computer program product are provided according to the present invention for determining the percent transmittance of a vessel in response to illumination by light of each of a number of different wavelengths and, in turn, for determining the oxygen saturation of blood within the vessel. The method, apparatus and computer program product of the present invention can create a map of the blood oxygen saturation within the vessel and can provide statistics based upon the blood oxygen saturation map. While the method, apparatus and computer program product of the present invention are useful in a variety of contexts, the method, apparatus and computer program product of the present invention are particularly useful to analyze images of retinal vessels having relatively low contrast in which it is otherwise difficult to reliably distinguish the retinal vessel from the background fundus, i.e., the tissue bed underlying the retinal vessel. In this regard, the method, apparatus and computer program product of the present invention are particularly useful in analyzing the images created by optical signals having a wavelength in the red spectrum and images created based upon single pass light that has been preferentially filtered by an aperture or the like, as described in U.S. patent application Ser. No. 10/134,360. However, the method, apparatus and computer program product of the present invention can be utilized to analyze images of other vessels lying upon a tissue bed, such as the vessels found underneath the tongue and vessels examined endoscopically, in which it is desirable to distinguish the vessel from the tissue bed. For the purposes of explanation but not of limitation, the method, apparatus and computer program product of the present invention will be hereinafter described in conjunction with the analysis of images of retinal vessels and the background fundus, i.e., the tissue bed, upon which the retinal vessels lie.

As depicted in FIG. 1, the method, apparatus and computer program product of the present invention generally includes multiple steps as subsequently explained in detail. Once the images are obtained with light of several different wavelengths, these steps include: optionally filtering the images, determining the vessel of interest within each image, registering (aligning) the images that are acquired at different wavelengths (if needed), identifying the pixels of each image that correspond to the vessel versus those that correspond to the tissue bed, filling-in the vessel pixels of each image such that the vessel is indistinguishable from the tissue bed, dividing each original image by the corresponding filled-in image to determine the percent transmittance of the vessel, determining oxygen saturation from the multi-spectral transmittance values for each pixel that corresponds to the vessel, and presenting an oxygen saturation image and determining statistics from the saturation data.

As shown in block 10 of FIG. 1, the images of the posterior portion of the eye are initially examined to determine the retinal vessel of interest within the image. While the images can be obtained in a variety of different manners, the images are typically obtained by illuminating the posterior portion of the eye with light having a plurality of different wavelengths as described by U.S. Pat. No. 6,244,712. The images may then be filtered to reduce the noise, if desired. Various techniques can be utilized to filter the images including median filtering and Fourier transform filtering as known to those skilled in the art. Once any desired filtering has been completed, the retinal vessel can be identified in a variety of manners known to those skilled in the art. See, for example, Adam Hoover, V. Kouznetsova and M. Goldbaum, "Locating Blood Vessels in Retinal Images by Piecewise Threshold Probing of a Matched Filter Response," *IEEE Trans. Med. Imaging*, 19(3) (2000); Y A. Tolias and S M. Panas, "A Fuzzy Vessel Tracking Algorithm for Retinal Images Based on Fuzzy Clustering," *IEEE Trans. Med. Imaging*, 17(2) (1998); S. Chaudhuri, S. Chaterjee, Norman Katz, Mark Nelson and Michael Goldbaun, "Detection of Blood Vessels in Retinal Images Using Two-Dimensional matched Filters," *IEEE Trans. Med. Imaging*, 8(3) (1989). While the automated procedures described in the foregoing references advantageously isolate each of the vessels within an image for further analysis, an operator may also manually select a retinal vessel for further examination from among the retinal vessels in an image by placing the cursor upon the desired retinal vessel in the image and thereafter selecting the retinal vessel. In this regard, the placement of the cursor serves to position or define a region including a portion of the retinal vessel for further analysis, as shown by the white rectangles in FIG. 2. While each retinal vessel, including both arteries and veins, may be identified within the images and thereafter analyzed either concurrently or separately, the method, apparatus and computer program product of the present invention can also analyze a single retinal vessel. For purposes of explanation, the method, apparatus and computer program product will be hereinafter described in conjunction with the selection and examination of a single retinal vessel without concurrently examining other retinal vessels in the image.

Once the retinal vessel of interest has been identified as depicted by the white rectangles in FIG. 2, the spectroscopic images are aligned or registered with respect to one another as shown in block 20 of FIG. 1. In this regard, the images are registered such that a pixel corresponding to a specific location within the retinal vessel in one image corresponds to the same location within the retinal vessel in each of the other images. The images can be registered in any manner known to those skilled in the art, such as that described by F. Zana and J. C. Klein, "A Multimodal Registration Algorithm of Eye Fundus Images Using Vessels Detection and Hough Transform," *IEEE Trans. Med. Imaging*, 18(5) (1999). As a result of the registration, the unregistered images of the retinal vessel of interest depicted in the left-hand column of FIG. 3 will be aligned with respect to one another as depicted in the right-hand column of FIG. 3.

Following the registration, each image is analyzed to identify the pixels that are representative of the retinal vessel as opposed to the pixels that are representative of the background fundus, even in instances in which the contrast between the retinal vessel and the background fundus is low. See block 30 of FIG. 1. In this regard, the pixels that correspond to the retinal vessel generally have a lower intensity and, accordingly, are darker than pixels that represent the background fundus. Unfortunately, the appearance of the retinal vessels relative to the background fundus can vary dramatically from one image to the next depending upon the wavelength of light at which the images were captured. In this regard, the retinal vessel contrast and irregularities in the fundus pigmentation, i.e., freckles and the like, in an image captured at one wavelength can differ significantly the retinal vessel contrast and irregularities in the fundus pigmentation captured at another wavelength. As such, the technique for identifying the pixels that correspond to the retinal vessel must accurately identify the retinal vessel in each monochromatic image despite these variations with the wavelength of light at which the images were captured.

According to one technique, a simple thresholding technique could be applied to each of the monochromatic images. In this technique, a threshold level may be determined as a predetermined fraction of the mean pixel value in an image. Thereafter, all pixels of the image having values below the threshold could be considered as pixels that represent the retinal vessel, while all pixels having a value above the threshold could be considered as pixels that represent the background fundus.

While the foregoing technique may be effective, the method, apparatus and computer program product of the present invention may also utilize other techniques for distinguishing between pixels representative of the retinal vessel and pixels representative of the background fundus with more certainty. In this regard, it has been determined that the coloration of the fundus tends to vary most significantly in the direction along the retinal vessel or, more generally, parallel to the retinal vessel. As such, the thresholding technique may be applied, not to all of the pixels in a monochromatic image simultaneously as described above, but on a line-by-line basis. As used herein, a line of the image can have a width or thickness of greater than one pixel if desired, such as a width of two, three or more pixels. In this regard, the mean $\bar{x}$ and the standard deviation $\sigma_x$ of the pixels in a single line of a monochromatic image taken in a direction generally perpendicular to the retinal vessel are determined. A threshold value x is then determined based upon a predetermined fraction $\alpha$ of the standard deviation as follows:

$$x = \bar{x} - \alpha \sigma_x$$

Thereafter, all pixels in the line perpendicular to the retinal vessel that have values lower than x are considered to be representative of the retinal vessel, while all pixels in the line having values greater than x are considered to be representative of the background fundus. The predetermined fraction $\alpha$ will depend upon wavelength selection and instrument configuration. However, in one configuration in which images were obtained with the light having wavelengths of 488 nm, 635 nm, 670 nm and 830 nm, a predetermined fraction $\alpha$ of 0.2 was utilized. By separately analyzing each line of an image in a direction perpendicular to the retinal vessel, new images can be created in which the retinal vessels are depicted in one color, and the background is depicted in another color. For example, FIG. 4 depicts the images of the retinal vessel following the line-by-line thresholding procedure in which the black areas correspond to pixels that are expected to represent a retinal vessel, while the white areas correspond to pixels that are expected to represent the background fundus.

As will be noted, a number of pixels are black that should be representative of the background fundus. In order to more correctly classify all the pixels, the images of FIG. 4 are further processed. While the method, apparatus and computer program product of the present invention can process the images in various manners, one advantageous technique for processing the images will be hereinafter described for purposes of illustration, but not of limitation. In this regard, a pulse coupled neural network can be employed to further process the images, such as those depicted in FIG. 4. The pulse coupled neural network effectively operates by examining each pixel of the images of FIG. 4 that is depicted to be representative of the retinal vessel, i.e., every black pixel, and determining if the other pixels in the neighborhood of a respective black pixel are also currently depicted to be representative of a retinal vessel. If at least a portion and, more preferably, all of the surrounding pixels are instead representative of the background fundus, the pulse coupled neural network will change the respective pixel to be representative of the background fundus as well. If, however, the other pixels in the neighborhood are also representative of the retinal vessel, the pulse coupled neural network will permit the pixel to remain representative of the retinal vessel. Further details of a pulse coupled neural network are provided by G. Kuntimad, et al., "Perfect Images Segmentation using Pulse Coupled Neural Networks," *IEEE Trans. Neural Net.*, 10(3), 591–598 (1999). Following the application of the pulse coupled neural network, the images of FIG. 4 are converted to the images of FIG. 5.

As shown in FIG. 5, however, a number of pixels remote from the retinal vessel may still be depicted to be representative of a retinal vessel following the further processing provided by the pulse coupled neural network. In addition, the images acquired with light of a different wavelength, such as the four images of FIG. 5, may not agree with one another as to the exact boundary between the retinal vessel and the background fundus. In order to address each of these issues, the method, apparatus and computer program product of the present invention may implement a voting algorithm. In accordance with the voting algorithm, the corresponding pixels of each of the four images are examined on a pixel-by-pixel basis to determine if a particular pixel should be representative of the retinal vessel or the background fundus. In one advantageous embodiment, the pixel is set to be representative of the background fundus in each of the four images if the respective pixel is representative of the background fundus in three or more of the four images of FIG. 5. Otherwise, the pixel is set to be representative of a retinal vessel in all four images. In other words, a pixel is set to be representative of a retinal vessel in each of the four images if, and only if, the pixel is representative of a retinal vessel in at least two of the images of FIG. 5. Following the application of the voting algorithm, the images of FIG. 6 are produced. As will be apparent, the criteria utilized by the voting algorithm may be varied if desired.

Finally, pixels that are far removed from the center of the retinal vessel, such as pixels along the edge of the images, may still appear to be representative of the retinal vessel. In this regard, the further from a retinal vessel that a pixel lies, the more likely the pixel is to be falsely representative of a retinal vessel due to reflectance variations of the background fundus. In addition, if the region originally selected for examination by the operator, i.e., the region in the white rectangle of FIG. 2, also includes a portion of a second vessel, then at least some of the pixels along the edge of the image are also likely to be properly identified as a retinal vessel as shown in FIGS. 3–6. While multiple retinal vessels may be examined concurrently, the embodiment of the method, apparatus and computer program product of the present invention that is described for purposes of illustration analyzes a single retinal vessel at a time. As such, the images of FIG. 6 are further processed in order to further clean the edges of the images. One technique for further processing the images is a blob analysis as known to those skilled in the art. In this regard, the blob is the retinal vessel of interest represented by a group of adjacent pixels that have each been identified to represent the vessel. In order to further clean the images, the method, apparatus and computer program product of the present invention begin at the centroid of the blob and identify the first line of pixels on each opposed side of the retinal vessel that is composed entirely of pixels representative of the background fundus, i.e., the first line of white pixels to the left and right of the retinal vessel in the illustrated embodiment. Typically, these lines of pixels are disposed in a generally parallel alignment with the vessel. Any pixels that lie beyond the lines of pixels representative of the background fundus are set to be representative of the background fundus, thereby cleaning up any pixels along the edges of the images that are otherwise representative of a retinal vessel. The resulting images created by this blob analysis are depicted in FIG. 7.

Once the pixels representative of the retinal vessel have been properly separated from the pixels that are representative of the background fundus, background images of the background fundus underlying the retinal vessel are created by scaling the pixels that correspond to the retinal vessel such that they have the same appearance as the pixels representative of the background. In other words, the images are processed to depict, not the retinal vessel, but the background fundus underlying the retinal vessel. The method, apparatus and computer program product of the present invention can scale the pixels representative of the retinal vessel according to a variety of techniques. For each respective image, for example, the method, apparatus and computer program product of the present invention can analyze the pixels representative of the background fundus on either side of the retinal vessel and thereafter fit curves to the pixels representative of the background fundus on either side of the retinal vessel in order to approximate the background fundus that underlies the retinal vessel. The curve fitting technique may employ any desired type of curve including any type of analytic function and any type of fractal function.

Alternatively, the method, apparatus and computer program product can employ a histogram equalization technique for each respective image such that the pixels that are representative of the retinal vessel are scaled by multiplicative and additive factors such that their respective intensity histograms have the same mean and standard deviation as the intensity histograms for the pixels representative of the background fundus. In this regard, the left-hand column of FIG. 8 depicts intensity histograms for the four images obtained at different respective wavelengths. The histograms that have cross-hatching sloping upwardly and to the right are constructed based upon the pixel values for those pixels representative of the retinal vessel, while the histograms that have cross-hatching sloping downwardly and to the right are constructed based upon the pixel values for those pixels representative of the background fundus. In determining the pixels that are representative of the retinal vessel and the pixels that are representative of the background fundus, the images of FIG. 7 are utilized. In determining the pixel values, however, the registered images of FIG. 3 are utilized since the images of FIG. 3 still contain a range of pixel values. Following an analysis of the intensity histograms representative of the retinal vessels and the background fundus, the values of the pixels representative of the retinal vessel for a respective image are altered by a multiplicative and additive process such that the mean and standard deviation of the values of the pixels corresponding to the retinal vessel are scaled to equal those of the pixels representative of the background fundus for the same respective image. The histograms that have cross-hatching sloping upwardly and to the right in the right hand column of FIG. 8 correspond to the four images captured with light of different wavelengths and are representative of the distribution of the values of the pixels formerly representative of the retinal vessel following the scaling such that the mean and standard deviation of the pixels formerly representative of the retinal vessels and the pixels representative of the background fundus are equal. As will be noted, the histograms that have cross-hatching sloping downwardly and to the right in the right hand column of FIG. 8 still represent the pixels representative of the background fundus and are identical to the gray histograms in the left hand column since the value of those pixels has not changed.

The pixels that represent the retinal vessel may be scaled in still other manners. For example, the shape of the vessel may be taken into account in scaling the pixels. In this regard, a vessel may be considered to be cylindrical or, more typically, elliptical. As such, the vessel is thinner proximate the opposed edges and thicker in medial portions. If the value of all of the pixels that represent the retinal vessel are scaled in the same manner, so as to have the same mean and standard deviation, for example, the values of the pixels representative of the edges of the vessel may be increased too much while the pixels representative of medial portions of the vessel may not be increased enough, thereby creating a filled-in background image having brighter portions coincident with the edges of the vessel. By taking the shape of the vessel into account, the values of the pixels need not be altered in a uniform manner across the width of the vessel, but, instead, the value of the pixels may be adjusted in accordance with a direct relationship to the shape of the vessel such that a pixel representative of the edge of a vessel is altered to a lesser degree than a pixel representative of a medial portion f the vessel. Thus, the resulting filled in background image should more accurately represent the background fundus.

Once the value of the pixels formerly representative of the retinal vessel have been rescaled as shown in the right hand column of FIG. 8, for example, the resulting images (termed "background images") have been effectively filled in such that that portion of the images that formerly depicted the retinal vessel now approximate the background fundus that underlies the retinal vessel. See block 40 of FIG. 1. In this regard, FIG. 9 depicts the original registered images in the left hand column and the filled in background images following scaling of the pixels formerly representative of the retinal vessels in the center column. The method, apparatus and computer program product of the present invention then divide each filled in background image into the corresponding original image on a pixel-by-pixel basis to determine the transmittance images as depicted in the right hand column of FIG. 9. See block 50 of FIG. 1. As shown, the pixels representative of the background fundus on opposite sides of the retinal vessel will have a transmittance value equal to one since the original registered image and the filled in image each have the same values for these pixel locations. However, the pixels representative of the retinal vessel will have transmittance values that may vary since a pixel representing a retinal vessel will generally be darker and, therefore, have a smaller value than a corresponding pixel representing the tissue bed or background fundus underlying the retinal vessel.

Based upon the transmittance images at each of the different wavelengths as shown in FIG. 9, the oxygen saturation of the blood within the retinal vessel can then be determined on a pixel-by-pixel basis. See block 60 of FIG. 1. As described in more detail in U.S. Pat. No. 5,776,060, the values of the corresponding pixels in each of the transmittance images together with the wavelengths at which the images were acquired are analyzed to determine the blood oxygen saturation. Since the analysis is performed on a pixel-by-pixel basis, a map of the blood oxygen saturation values can be presented graphically as shown in FIG. 10 in which different percentages of blood oxygen saturation are depicted by different colors as shown by the scale on the right hand side of FIG. 10. By presenting the blood oxygen saturation as a map, the image may reveal variations in blood oxygen saturation along the length of the vessel or across the diameter of the vessel that may prove useful during subsequent analysis and diagnosis. In addition or alternatively, the method, apparatus and computer program product of the present invention can perform a statistical analysis of the values of all of the pixels that form the saturation image to determine various statistics such as the mean, standard deviation and standard error of the mean. These parameters may further assist in the analysis of the blood oxygen saturation since variations due to fundus pigmentation can be averaged out. These parameters also provide a measure of the uncertainty of the mean saturation value which may serve as a discriminant for accepting or rejecting a given measurement.

As such, the method, apparatus and computer program product of the present invention provide an improved technique for processing multispectral images of a vessel, such as a retinal vessel, to determine the percent transmittance of the vessel in response to illumination by light of each of a number of different wavelengths and, in turn, the blood oxygen saturation within the vessel. As a result of the innovative processing techniques, the method, apparatus and computer program product of the present invention is particularly well suited for analyzing images that have a relatively low contrast between the retinal vessel and the background fundus, such as images created by light having a wavelength in the red spectrum and images created by single pass signals that have been preferentially filtered by an aperture or the like. Moreover, although the method, apparatus and computer program product of the present invention has been described in conjunction with the identification and analysis of a single vessel, the method, apparatus and computer program product can also identify and analyze all vessels within an image and can determine the blood oxygen saturation within each vessel. As such, the method, apparatus and computer program product of this embodiment can present an image of the blood oxygen saturation in each vessel, thereby permitting arteries and veins to be separately identified based upon the higher blood oxygen saturation of the arteries relative to the veins and further permitting average arterial and venous blood oxygen saturation values to be determined.

The method and apparatus of the present invention can be implemented in a variety of manners, but is typically implemented by a combination of hardware, software and/or firmware that performs each of the various operations described above. For example, the method and apparatus may be implemented by one or more computer processing elements, such as a specially programmed computer. The computer processing element(s) typically operate under the control of a computer program product. The computer program product includes a computer-readable storage medium, such as a non-volatile storage medium, and computer-readable program code portions, such as a series of computer instructions, embodied in the computer-readable storage medium. Typically, the computer program product is stored by the computer processing element(s) or a related memory device. In addition to the computer program product for appropriately directing operation of the computer processing element(s), the apparatus of the present invention generally includes the display for depicting the various images and an input device, such as a keyboard and/or a mouse, for permitting operator input at various stages of the process.

As described above, FIG. 1 is a block diagram and control flow illustration of a method, apparatus and program product according to one embodiment of the invention. It will be understood that each block or step of the block diagram, flowchart and control flow illustration, and combinations of blocks in the block diagram, flowchart and control flow illustration, can be implemented by computer program instructions. These computer program instructions may be loaded onto a computer or other programmable apparatus to produce a machine, such that the instructions which execute on the computer or other programmable apparatus create means for implementing the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the block diagram, flowchart or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

Accordingly, blocks or steps of the block diagram or control flow illustration support combinations of means for performing the specified functions, combinations of steps for performing the specified functions and program instruction means for performing the specified functions. It will also be understood that each block or step of the block diagram, flowchart or control flow illustration, and combinations of blocks or steps in the block diagram, flowchart or control flow illustration, can be implemented by special purpose hardware-based computer systems which perform the specified functions or steps, or combinations of special purpose hardware and computer instructions.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for determining blood oxygen saturation in a vessel based upon a plurality of images of the vessel obtained in response to illumination of the vessel at different wavelengths, each image being comprised of a plurality of pixels, the method comprising:
   generating a plurality of background images based upon respective ones of the plurality of images of the vessel, wherein generating the background images comprises approximating an image of a tissue bed underlying the vessel based upon a combination of pixels representative of the vessel and pixels representative of the tissue bed proximate to the vessel;
   determining a plurality of transmittance images based upon respective pairs of the background images and the images of the vessel; and
   determining the blood oxygen saturation in the vessel based upon the plurality of transmittance images.

2. A method according to claim 1 further comprising identifying at least one vessel in each of the images of the vessel prior to generating the background images.

3. A method according to claim 1 further comprising registering the vessel in each of the images of the vessel prior to generating the background images.

4. A method according to claim 1 wherein the method further comprises processing the plurality of images of the vessel to separate, within each image, pixels representative of the vessel from pixels representative of the tissue bed.

5. A method according to claim 1 wherein generating the plurality of background images comprises scaling the pixels representative of the vessel to have the same mean and standard deviation as the pixels representative of the tissue bed.

6. A method according to claim 1 wherein determining a plurality of transmittance images comprises dividing each image of the vessel by the respective background image.

7. A method according to claim 1 wherein determining the blood oxygen saturation in the vessel comprises generating an image of the blood oxygen saturation in the vessel.

8. A method for determining blood oxygen saturation in a vessel based upon a plurality of images of the vessel obtained in response to illumination of the vessel at different wavelengths, each image being comprised of a plurality of pixels, the method comprising:
   processing the plurality of images of the vessel to separate, within each image, pixels representative of the vessel from pixels representative of a tissue bed, wherein processing the plurality of images of the vessel comprises separately analyzing the pixels of each image along respective lines extending across the vessel to separate the pixels along the respective lines into pixels representative of the vessel and pixels representative of the tissue bed;
   generating a plurality of background images based upon respective ones of the plurality of images of the vessel, wherein generating the background images comprises approximating an image of the tissue bed underlying the vessel;
   determining a plurality of transmittance images based upon respective pairs of the background images and the images of the vessel; and
   determining the blood oxygen saturation in the vessel based upon the plurality of transmittance images.

9. A method for determining blood oxygen saturation in a vessel based upon a plurality of images of the vessel obtained in response to illumination of the vessel at different wavelengths, wherein each image is comprised of a plurality of pixels, the method comprising:
   processing each image to identify pixels representative of the vessel that are at least partially surrounded by pixels representative of a tissue bed and to redefine any pixels that are so identified to be representative of the tissue bed;
   generating a plurality of background images based upon respective ones of the plurality of images of the vessel, wherein generating the background images comprises approximating an image of the tissue bed underlying the vessel;
   determining a plurality of transmittance images based upon respective pairs of the background images and the images of the vessel; and
   determining the blood oxygen saturation in the vessel based upon the plurality of transmittance images.

10. for determining blood oxygen saturation in a vessel based upon a plurality of images of the vessel obtained in response to illumination of the vessel at different wavelengths, wherein each image is comprised of a plurality of pixels, the method comprising:

processing the plurality of images to identify a pixel in one image that differs from a corresponding pixel in another image in its representation of that portion of the image as either the vessel or a tissue bed and to redefine one of the pixels to be consistent with the other pixel;

generating a plurality of background images based upon respective ones of the plurality of images of the vessel, wherein generating the background images comprises approximating an image of the tissue bed underlying the vessel;

determining a plurality of transmittance images based upon respective pairs of the background images and the images of the vessel; and determining the blood oxygen saturation in the vessel based upon the plurality of transmittance images.

11. A method for determining blood oxygen saturation in a vessel based upon a plurality of images of the vessel obtained in response to illumination of the vessel at different wavelengths, wherein each image is comprised of a plurality of pixels, the method comprising:

processing the plurality of images to identify a group of adjacent pixels that each represent the vessel and to redefine any pixels that are also initially representative of the vessel but are remote from the group of adjacent pixels to be representative of a tissue bed;

generating a plurality of background images based upon respective ones of the plurality of images of the vessel, wherein generating the background images comprises approximating an image of the tissue bed underlying the vessel;

determining a plurality of transmittance images based upon respective pairs of the background images and the images of the vessel; and determining the blood oxygen saturation in the vessel based upon the plurality of transmittance images.

12. A method for determining blood oxygen saturation in a vessel based upon a plurality of images of the vessel obtained in response to illumination of the vessel at different wavelengths, wherein each image is comprised of a plurality of pixels, the method comprising:

generating a plurality of background images based upon respective ones of the plurality of images of the vessel, wherein generating the background images comprises approximating an image of a tissue bed underlying the vessel, and wherein generating the plurality of background images comprises scaling the pixels representative of the vessel based upon a shape of the vessel;

determining a plurality of transmittance images based upon respective pairs of the background images and the images of the vessel; and determining the blood oxygen saturation in the vessel based upon the plurality of transmittance images.

13. A method for determining blood oxygen saturation in a vessel based upon a plurality of images of the vessel obtained in response to illumination of the vessel at different wavelengths, wherein each image is comprised of a plurality of pixels, the method comprising:

generating a plurality of background images based upon respective ones of the plurality of images of the vessel, wherein generating the background images comprises approximating an image of a tissue bed underlying the vessel, and wherein generating the plurality of background images comprises redefining the pixels that formerly represented the vessel in accordance with curves that are fit based upon values of the pixels representative of the tissue bed that are on opposite sides of the pixels representative of the vessel;

determining a plurality of transmittance images based upon respective pairs of the background images and the images of the vessel; and determining the blood oxygen saturation in the vessel based upon the plurality of transmittance images.

14. An apparatus for determining blood oxygen saturation in a vessel based upon a plurality of images of the vessel obtained in response to illumination of the vessel at different wavelengths, each image being comprised of a plurality of pixels, the apparatus comprising a processing element capable of generating a plurality of background images based upon respective ones of the plurality of images of the vessel, wherein said processing element is capable of generating the background images by approximating an image of a tissue bed underlying the vessel based upon a combination of pixels representative of the vessel and pixels representative of the tissue bed proximate to the vessel, wherein said processing element is also capable of determining a plurality of transmittance images based upon respective pairs of the background images and the images of the vessel, and wherein said processing element is further capable of determining the blood oxygen saturation in the vessel based upon the plurality of transmittance images.

15. An apparatus according to claim 14 wherein said processing element is further capable of registering the vessel in each of the images of the vessel prior to generating the background images.

16. An apparatus according to claim 14 wherein said processing element is further capable of processing the plurality of images of the vessel to separate, within each image, pixels representative of the vessel from pixels representative of the tissue bed.

17. An apparatus according to claim 16 wherein said processing element is capable of processing the plurality of images of the vessel by separately analyzing the pixels of each image along respective lines extending across the vessel to separate the pixels along the respective lines into pixels representative of the vessel and pixels representative of the tissue bed.

18. An apparatus according to claim 14 wherein said processing element is further capable of processing each image to identify pixels representative of the vessel that are at least partially surrounded by pixels representative of the tissue bed and to redefine any pixels that are so identified to be representative of the tissue bed.

19. An apparatus according to claim 14 wherein said processing element is further capable of processing the plurality of images to identify a pixel in one image that differs from a corresponding pixel in another image in its representation of that portion of the image as either the vessel or the tissue bed and to redefine one of the pixels to be consistent with the other pixel.

20. An apparatus according to claim 14 wherein said processing element is further capable of processing the plurality of images to identify a group of adjacent pixels that each represent the vessel and to redefine any pixels that are also initially representative of the vessel but are remote from the group of adjacent pixels to be representative of the tissue bed.

21. An apparatus according to claim 14 wherein said processing element is capable of generating the plurality of background images by scaling the pixels representative of the vessel to have the same mean and standard deviation as the pixels representative of the tissue bed.

22. An apparatus according to claim 14 wherein said processing element is capable of determining a plurality of transmittance images by dividing each image of the vessel by the respective background image.

23. An apparatus according to claim 14 wherein said processing element is further capable of generating an image of the blood oxygen saturation in the vessel.

24. An apparatus for determining blood oxygen saturation in a vessel based upon a plurality of images of the vessel obtained in response to illumination of the vessel at different wavelengths, wherein each image is comprised of a plurality of pixels, the apparatus comprising a processing element capable of generating a plurality of background images based upon respective ones of the plurality of images of the vessel, wherein said processing element is capable of generating the background images by approximating an image of a tissue bed underlying the vessel, and wherein said processing element is capable of generating the plurality of background images by scaling the pixels representative of the vessel based upon a shape of the vessel, wherein said processing element is also capable of determining a plurality of transmittance images based upon respective pairs of the background images and the images of the vessel, and wherein said processing element is further capable of determining the blood oxygen saturation in the vessel based upon the plurality of transmittance images.

25. An apparatus for determining blood oxygen saturation in a vessel based upon a plurality of images of the vessel obtained in response to illumination of the vessel at different wavelengths, wherein each image is comprised of a plurality of pixels, the apparatus comprising a processing element capable of generating a plurality of background images based upon respective ones of the plurality of images of the vessel, wherein said processing element is capable of generating the background images by approximating an image of a tissue bed underlying the vessel, and wherein said processing element is capable of generating the plurality of background images by redefining the pixels that formerly represented the vessel in accordance with curves that are fit based upon values of the pixels representative of the tissue bed that are on opposite sides of the pixels representative of the vessel, wherein said processing element is also capable of determining a plurality of transmittance images based upon respective pairs of the background images and the images of the vessel, and wherein said processing element is further capable of determining the blood oxygen saturation in the vessel based upon the plurality of transmittance images.

26. A computer program product for determining blood oxygen saturation in a vessel based upon a plurality of images of the vessel obtained in response to illumination of the vessel at different wavelengths, each image being comprised of a plurality of pixels, the computer program product comprising a computer-readable storage medium having computer-readable instructions embodied therein, the computer-readable instructions comprising:

first computer-readable instructions capable of generating a plurality of background images based upon respective ones of the plurality of images of the vessel, wherein said first computer-readable instructions are capable of generating the background images by approximating an image of a tissue bed underlying the vessel based upon a combination of pixels representative of the vessel and pixels representative of the tissue bed proximate to the vessel;

second computer-readable instructions capable of determining a plurality of transmittance images based upon respective pairs of the background images and the images of the vessel; and third computer-readable instructions capable of determining the blood oxygen saturation in the vessel based upon the plurality of transmittance images.

27. A computer program product according to claim 26 further comprising fourth computer-readable instructions capable of registering the vessel in each of the images of the vessel prior to generation of the background images by said first computer-readable instructions.

28. A computer program product according to claim 26 further comprising fifth computer-readable instructions capable of processing the plurality of images of the vessel to separate, within each image, pixels representative of the vessel from pixels representative of the tissue bed.

29. A computer program product according to claim 28 wherein said fifth computer-readable instructions are capable of separately analyzing the pixels of each image along respective lines extending across the vessel to separate the pixels along the respective lines into pixels representative of the vessel and pixels representative of the tissue bed.

30. A computer program product according to claim 26 further comprising fifth computer-readable instructions capable of processing each image to identify pixels representative of the vessel that are at least partially surrounded by pixels representative of the tissue bed and to redefine any pixels that are so identified to be representative of the tissue bed.

31. A computer program product according to claim 26 further comprising fifth computer-readable instructions capable of processing the plurality of images to identify a pixel in one image that differs from a corresponding pixel in another image in its representation of that portion of the image as either the vessel or the tissue bed and to redefine one of the pixels to be consistent with the other pixel.

32. A computer program product according to claim 26 further comprising fifth computer-readable instructions capable of processing the plurality of images to identify a group of adjacent pixels that each represent the vessel and to redefine any pixels that are also initially representative of the vessel but are remote from the group of adjacent pixels to be representative of the tissue bed.

33. A computer program product according to claim 26 wherein said first computer-readable instructions are further capable of scaling the pixels representative of the vessel to have the same mean and standard deviation as the pixels representative of the tissue bed.

34. A computer program product according to claim 26 wherein said second computer-readable instructions are further capable of dividing each image of the vessel by respective background image.

35. A computer program product according to claim 26 wherein said third computer-readable instructions are further capable of generating an image of the blood oxygen saturation in the vessel.

36. A computer program product for determining blood oxygen saturation in a vessel based upon a plurality of images of the vessel obtained in response to illumination of the vessel at different wavelengths, wherein each image is comprised of a plurality of pixels, the computer program product comprising a computer-readable storage medium having computer-readable instructions embodied therein, the computer-readable instructions comprising:

first computer-readable instructions capable of generating a plurality of background images based upon respective ones of the plurality of images of the vessel, wherein said first computer-readable instructions are capable of generating the background images by approximating an image of a tissue bed underlying the vessel, and wherein said first computer-readable instructions are further capable of scaling the pixels representative of the vessel based upon a shape of the vessel;

second computer-readable instructions capable of determining a plurality of transmittance images based upon respective pairs of the background images and the images of the vessel; and third computer-readable instructions capable of determining the blood oxygen saturation in the vessel based upon the plurality of transmittance images.

37. A computer program product for determining blood oxygen saturation in a vessel based upon a plurality of images of the vessel obtained in response to illumination of the vessel at different wavelengths, wherein each image is comprised of a plurality of pixels, the computer program product comprising a computer-readable storage medium having computer-readable instructions embodied therein, the computer-readable instructions comprising:

first computer-readable instructions capable of generating a plurality of background images based upon respective ones of the plurality of images of the vessel, wherein said first computer-readable instructions are capable of generating the background images by approximating an image of a tissue bed underlying the vessel, and wherein said first computer-readable instructions are further capable of redefining the pixels that formerly represented the vessel in accordance with curves that are fit based upon values of the pixels representative of the tissue bed that are opposite sides of the pixels representative of the vessel;

second computer-readable instructions capable of determining a plurality of transmittance images based upon respective pairs of the background images and the images of the vessel; and third computer-readable instructions capable of determining the blood oxygen saturation in the vessel based upon the plurality of transmittance images.

38. A method for generating a background image based upon an image of the vessel obtained in response to illumination of the vessel at a respective wavelength, the method comprising:

processing the image of the vessel to separate pixels representative of the vessel from pixels representative of a tissue bed; and redefining the pixels that formerly represented the vessel based upon a combination of respective values of at least some of the pixels that formerly represented the vessel and at least some of the pixels representative of the tissue bed to create the background image, wherein the background image at least partially represents the tissue bed that underlies the vessel.

39. A method according to claim 38 wherein redefining the pixels that formerly represented the vessel comprises scaling the pixels representative of the vessel to have the same mean and standard deviation as the pixels representative of the tissue bed.

40. A method according to claim 38 wherein processing the plurality of images of the vessel comprises separately analyzing the pixels along respective lines extending across the vessel to separate the pixels along the respective lines into pixels representative of the vessel and pixels representative of the tissue bed.

41. A method according to claim 38 further comprising processing the image to identify pixels representative of the vessel that are at least partially surrounded by pixels representative of the tissue bed and to redefine any pixels that are so identified to be representative of the tissue bed, prior to the redefining step.

42. A method according to claim 38 further comprising processing the image to identify a group of adjacent pixels that each represent the vessel and to redefine any pixels that are also initially representative of the vessel but are remote from the group of adjacent pixels to be representative of the tissue bed.

43. A method according to claim 38 wherein a plurality of background images of the vessel are generated based upon a plurality of images of the vessel obtained in response to illumination of the vessel at different wavelengths, and wherein the method further comprises registering the vessel in each of the images of the vessel prior to processing the plurality of images of the vessels.

44. A method according to claim 43 further comprising processing each image to identify a pixel in one image that differs from a corresponding pixel in another image in its representation of that portion of the image as either the vessel or the tissue bed and to redefine one of the pixels to be consistent with the other pixel.

45. A method for generating a background image based upon an image of the vessel obtained in response to illumination of the vessel at a respective wavelength, the method comprising:

processing the image of the vessel to separate pixels representative of the vessel from pixels representative of a tissue bed; and redefining the pixels that formerly represented the vessel based upon respective values of at least some of the pixels representative of the tissue bed to create the background image, wherein redefining the pixels that formerly represented the vessel comprises scaling the pixels representative of the vessel based upon a shape of the vessel, wherein the background image at least partially represents the tissue bed that underlies the vessel.

46. A method for generating a background image based upon an image of the vessel obtained in response to illumination of the vessel at a respective wavelength, the method comprising:

processing the image of the vessel to seperate pixels representative of the vessel from pixels representative of a tissue bed; and redefining the pixels that formerly represented the vessel based upon respective values of at least some of the pixels representative of the tissue bed to create the background image, wherein redefining the pixels that formerly represented the vessel comprises redefining the pixels that formerly represented the vessel in accordance with curves that are fit based upon values of the pixels representative of the tissue bed that are on opposite sides of the pixels representative of the vessel, wherein the background image at least partially represents the tissue bed that underlies the vessel.

47. A method of separating pixels representative of a vessel from pixels representative of a tissue bed in an image comprised of a plurality of pixels, wherein the method comprises:

examining the pixels along a plurality of lines that extend across the vessel;

determining, for each line of pixels, a threshold based upon values of the pixels along the respective line, wherein determining the threshold for each line of pixels comprises determining the threshold based upon at least one of a mean and a standard deviation of the values of the pixels along the respective line; and separating the pixels along each line into pixels representative of the vessel and pixels representative of the tissue bed depending upon a relationship of the threshold for the respective line to values of the pixels along the line.

48. A method according to claim 47 wherein examining the pixels comprises examining the pixels along a plurality of lines that extend perpendicular to the vessel.

49. A method according to claim 47 wherein determining the threshold for a respective line further comprises determining the threshold x as follows:

$$x = \bar{x} - \alpha \sigma_x$$

wherein $\bar{x}$ is the mean and $\sigma_x$ is the standard deviation of the pixels along the respective line, and wherein a is a predefined constant.

* * * * *

UNITED STATES PATENT AND TRADEMARK OFFICE
CERTIFICATE OF CORRECTION

PATENT NO. : 6,728,561 B2
DATED : April 27, 2004
INVENTOR(S) : Smith et al.

It is certified that error appears in the above-identified patent and that said Letters Patent is hereby corrected as shown below:

Column 14,
Line 66, insert -- A method -- at the beginning of the claim.

Signed and Sealed this

Twenty-seventh Day of July, 2004

JON W. DUDAS
*Acting Director of the United States Patent and Trademark Office*